(12) United States Patent
Ludwig

(10) Patent No.: US 7,436,514 B2
(45) Date of Patent: Oct. 14, 2008

(54) PROCESS ABSORPTION SPECTROMETER

(75) Inventor: Michael Ludwig, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 328 days.

(21) Appl. No.: 10/551,741

(22) PCT Filed: Apr. 1, 2004

(86) PCT No.: PCT/EP2004/003473

§ 371 (c)(1),
(2), (4) Date: Sep. 30, 2005

(87) PCT Pub. No.: WO2004/088289

PCT Pub. Date: Oct. 14, 2004

(65) Prior Publication Data

US 2006/0197039 A1   Sep. 7, 2006

(30) Foreign Application Priority Data

Apr. 1, 2003   (DE) ................. 103 14 793

(51) Int. Cl.
*G01N 21/00* (2006.01)
*H04B 10/00* (2006.01)

(52) U.S. Cl. ....................... 356/432; 398/140
(58) Field of Classification Search ....... None
See application file for complete search history.

(56) References Cited

U.S. PATENT DOCUMENTS

| 4,817,101 | A | | 3/1989 | Wyeth et al. |
| 4,935,875 | A | | 6/1990 | Shah et al. |
| 5,173,749 | A | * | 12/1992 | Tell et al. ................. 356/437 |
| 7,075,099 | B2 | * | 7/2006 | Buisker et al. ......... 250/559.36 |
| 2004/0168053 | A1 | * | 8/2004 | Kaszkin et al. ............. 713/153 |

FOREIGN PATENT DOCUMENTS

| DE | 101 58 745 A1 | 6/2003 |
| EP | 0 290 274 A1 | 11/1988 |
| WO | WO 02/095506 A2 | 11/2002 |

OTHER PUBLICATIONS

B. Engers and J. Schultz, J. Plitz, "Die Anbindung von Sensorsystemen an Feldbusse", Sensorik aktuell, Sonderausgabe, Nov. 2001, http://www.ama-sensorik.de/download/sensorik_sond_1101.pdf, pp. 8-9.
G.Y. Tian, Z.X. Zhao and R.W. Baines, "A Fieldbus-based intelligent sensor", Mechatronics, vol. 10, 2000, pp. 835-849, XP004201716.

* cited by examiner

*Primary Examiner*—Gregory J. Toatley, Jr.
*Assistant Examiner*—Amanda H Merlino

(57) ABSTRACT

The aim of the invention is to reduce the apparatus-related complexity and the mounting effort in a process absorption spectrometer taking in situ measurements. Said aim is achieved by providing the process absorption spectrometer with a unit comprising a source of radiation and at least one additional unit encompassing a detector, both units being embodied as pieces of field equipment and being connected to a field bus.

20 Claims, 1 Drawing Sheet

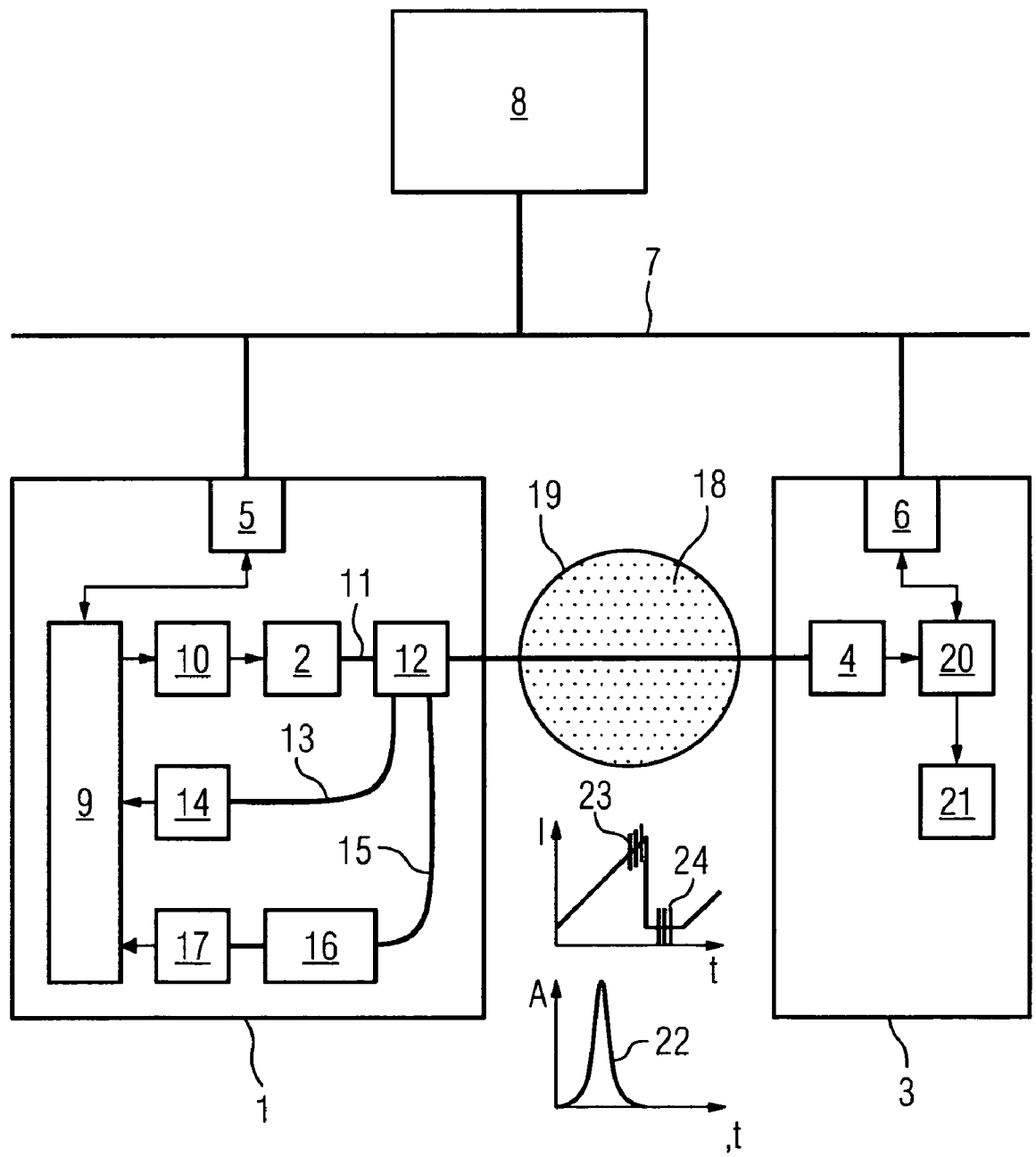

PROCESS ABSORPTION SPECTROMETER

CROSS REFERENCE TO RELATED APPLICATIONS

This application is the US National Stage of International Application No. PCT/EP2004/003473, filed Apr. 1, 2004 and claims the benefit thereof. The International Application claims the benefits of German application No. 10314793.4, filed Apr. 1, 2003, both applications are incorporated by reference herein in their entirety.

FIELD OF INVENTION

The invention relates to a process absorption spectrometer.

SUMMARY OF THE INVENTION

The principle of the absorption spectroscopy relates to the selective absorption of radiation of a specific wavelength by means of specific gases (gas molecules), in particular in the near infrared range (NIR). The radiation absorption results in the emergence of a spectrum which is characteristic for the gas in question. If a spectrometer is successfully selectively adjusted to the spectrum which is to be assigned to a specific gas, the received measurement signal is proportional to the number of molecules which are located in a measurement volume (measurement cell) between a source of radiation and a detector of the spectrometer. Methods known for industrial gas analysis are for instance non-dispersive infrared (NDIR) spectroscopy, Fourier transform infrared (FTIR) spectroscopy and diode laser spectroscopy.

With the so-called in-line measurement or in-situ measurement, the measurement cell of the spectrometer is either directly integrated into the measurement gas flow or the line carrying the measurement gas, e.g. a pipe or a chimney, functions itself as a measurement cell. The source of radiation and the detector, or several detectors in the case of multi-channel measurements, are thus arranged at different locations in the process plant, to which end the spectrometer is subdivided into two or more sub-devices. These sub-devices are connected to one another via special coupling lines, so that they can function as one complete device. The coupling lines and the signals passing over them are designed in this case to suit the specific technology or device (e.g. hybrid cable with electrical lines and fiber optic lines). The provision of and cable laying for this type of special lines involves a corresponding outlay.

The underlying object of the invention is thus to reduce the apparatus-related complexity and the mounting effort in in-situ absorption spectrometers.

According to the invention the object is achieved by means of a process absorption spectrometer having a unit containing a source of radiation and at least one additional unit containing a detector, both units being designed as pieces of field equipment and being connected to a field bus. As the units of the spectrometer according to the invention are designed as pieces of field equipment, they can be installed, parameterized and operated in a process plant and/or a process automation system in the same manner as any other pieces of field equipment without any additional effort. In particular, the cabling arrangements for them are standard as with other pieces of field equipment.

Corresponding to an advantageous development of the spectrometer according to the invention, the additional unit containing the detector contains means to generate a measurement result from measurement signals of the detector and additional signals, which are transmitted from the unit containing the source of radiation to the additional unit containing the detector. The additional signals can for example be reference signals which were acquired in the unit containing the source of radiation by reference measurement of a reference gas and are necessary for the generation of the measurement result.

These reference signals can be transmitted in an advantageous manner from the unit containing the source of radiation via the field bus to the additional unit containing the detector. This can be effected by a so-called slave-slave communication for instance. This function is one of those provided by the 'Profibus' field bus and can also be referred to as data cross-traffic. The communication between the units designed as pieces of field equipment and the process controller takes place according to the master-slave principle, i.e. a designated device is present in each instance in the process controller, said specially selected device being the master, which operates the field bus, parameterizes the slaves (pieces of field equipment) assigned to it and carries out the data exchange in a cyclical operation. In the case of the data cross-traffic, specific data, in this case additional signals, are not exchanged using the indirect route via the master, but instead directly between the slaves, thereby resulting in a reduced load on the master and a reduction in the time taken for the data transmission. The bus cycle does not significantly lengthen, any required mixture of master-slave and cross-traffic relationships is possible.

Alternatively or in addition to the transmission via the field bus, the source of radiation can be advantageously modulated with the additional signals, with the additional signals in the additional unit being separated from the measurement signals of the detector by means of demodulation. The modulation thus takes place such that the selective absorption of the radiation in the measurement gas is not impaired. By way of example, in the case of a diode laser spectrometer, with which a spectral line of the measurement gas is cyclically scanned in a wavelength dependent manner, the modulation with the additional signals can take place in an area of the scanning lying outside the spectral line or in the gaps between successive scanning cycles.

With a further embodiment of the spectrometer according to the invention, the means for generating the measurement result from the measurement signals of the detector can be arranged in the unit containing the source of radiation, in which case the measurement signals are transmitted from the additional unit containing the detector to the unit containing the source of radiation via the field bus.

The spectrometer according to the invention is described below with reference to an exemplary embodiment shown in the drawing.

BRIEF DESCRIPTION OF THE DRAWING

The sole FIG. 1 shows an exemplary embodiment of the inventive absorption spectrometer.

DETAILED DESCRIPTION OF INVENTION

The process absorption spectrometer shown as a greatly simplified block diagram comprises a unit 1 which comprises a continuously variable diode laser as a source of radiation 2, and a unit 3, which contains a photoelectrical detector 4. Both units 1 and 3 are designed respectively as pieces of field equipment and are connected via communication devices 5 and/or 6 to a field bus 7 in a process automation system of which only a master device 8 is shown here.

The unit 1 of the spectrometer further contains a controller device 9, which operates a modulation device 10 for wavelength-dependent modulation of the source of radiation 2. The light beam 11 emitted by the source of radiation 2 is fed to the detector 4 in the further unit 3 by means of a radiation divider 12 partially via a glass fiber 13 onto a monitor detector 14, via a further glass fiber 15 through a reference gas cell 16 filled with a reference gas onto a reference detector 17 and from the unit 1 through a measurement gas 18, in a pipe or chimney for instance. The measurement signals generated by the detector 4 are evaluated in an evaluation device 20 arranged downstream together with further signals to form a measurement result which is visualized on the one hand on a display 21 of the unit 3 and on the other hand is transmitted in the process automation system via the communication device 6. The additional signals mentioned, which are needed to generate the measurement result, are the reference signals of the reference detector 17, the monitor signals of the monitor detector 14 and information relating to the modulation of the source of radiation 2. These additional signals are generated in the unit 1 and are transmitted to the field bus 7 via the controller device 9 and the communication device 5 in order to receive the additional unit 3 from the communication device 6 and forward it to the evaluation device 20. The communication between the two units 1 and 3 thus takes place directly, i.e., by avoiding the master 8, according to a slave-slave transmission method also referred to as a data cross-traffic.

In addition or alternatively the additional signals can also be transmitted via the light beam 11 directly between the two units 1 and 3. The diagram shows how the source of radiation 2 is cyclically controlled by the modulation device 10 by means of a ramp-shaped increasing flow 1 in order to scan a spectral line 22 of the measurement gas 18 in a wavelength-dependent manner. The additional signals to be transmitted from the unit 1 to the unit 3 can then be remodulated in an area 23 of the scanning lying outside the spectral line 22 or in scanning gaps 24 between successive scannings.

Alternatively to the exemplary embodiment shown, the evaluation device 20 and the display device 21 can be arranged in the unit 1 containing the source of radiation 2, with which the measurement signals of the detector 4 are then transmitted from the additional unit 3 to the unit 1 containing the source of radiation 2 by means of the field bus 7.

The power can be supplied to units 1 and 3 separately or likewise via the field bus 7.

The invention claimed is:

1. A process absorption spectrometer for a gas comprising:
   a first unit containing a source of radiation, wherein the first unit is designed as a field device having a first communication device, and wherein the first unit is connectable to a field bus via the first communication device; and
   at least one second unit containing a detector, wherein the unit is designed as field device having second communication device, and wherein the second unit is connectable to the field bus via the second communication device.

2. The process absorbtion spectrometer according to claim 1, wherein the second unit comprises a mechanism to generate a measurement result from measurement signals of the detector and from signals transmitted from the first unit to the second unit, and wherein the signal are at least partially transmittable via the field bus.

3. The process absorption spectrometer according to claim 1, wherein the first and the second units are designed to communicate with one another via the field bus according to a slave-slave transmission method.

4. The process absorption spectrometer according to claim 1, wherein the source of radiation is modulated with at least one part of signals transmitted from the first unit to the second unit, and wherein in the second unit the signals transmitted from the first unit to the second unit are separated from measurement signals of the detector by demodulation.

5. The process absorption spectrometer according to claim 2, wherein the source of radiation is modulated with at least one part of signals transmitted from the first unit to the second unit, and wherein in the second unit the signals transmitted from the first unit to the second unit are separated from measurement signals of the detector using demodulation.

6. The process absorption spectrometer according to claim 1, wherein the source of radiation is modulated with at least one part of signals transmitted from the first unit to the second unit, and wherein in the second unit the signals transmitted from the first unit to the second unit are separated from measurement signals of the detector by using demodulation.

7. The process absorption spectrometer according to claim 3, wherein the source of radiation is modulated with at least one part of signals transmitted from the first unit to the second unit, and wherein in the second unit the signals transmitted from the first unit to the second unit are separated from measurement signals of the detector by demodulation.

8. The process absorption spectrometer according to claim 1, wherein the first unit comprises means for generating a measurement result from measurement signals of the detector, and wherein the measurement signals are transmittable from the second unit to the first unit via the field bus.

9. The process absorption spectrometer according to claim 2, wherein the first unit comprises means for generating a measurement result from measurement signals of the detector, and wherein the measurement signals are transmittable from the second unit to the first unit via the field bus.

10. The process absorption spectrometer according to claim 1, wherein the first unit comprises means for generating a measurement result from measurement signals of the detector, and wherein the measurement signals are transmittable from the second unit to the first unit via the field bus.

11. The process absorption spectrometer according to claim 3, wherein the first unit comprises means for generating a measurement result from measurement signals of the detector, and wherein the measurement signals are transmittable from the second unit to the first unit via the field bus.

12. The process absorption spectrometer according to claim 4, wherein the first unit comprises means for generating a measurement result from measurement signals of the detector, and wherein the measurement signals are transmittable from the second unit to the first unit via the field bus.

13. The process absorption spectrometer according to claim 1, wherein a power is supplied to the first unit via the field bus and a power is supplied to the second unit via the field bus.

14. A process absorption spectrometer, comprising:
   a first unit containing a source of radiation;
   a second unit containing a detector, wherein the first unit and the second units are separately connected to a field bus, wherein the field bus is connected to a mater device, wherein the master device is a process controller.

15. The process absorption spectrometer according to claim 14, wherein the additional unit containing the detector contains means to generate a measurement result from measurement signals of the detector and additional signals which are transmitted from the unit containing the source of radiation to the additional unit containing the detector.

16. The process absorption spectrometer according to claim 15, wherein the additional signals are at least partially transmitted via the field bus.

17. The process absorption spectrometer according to claim 16, wherein the two units communicate with one another via the field bus according to a slave-slave transmission method.

18. The process absorption spectrometer according to claim 14, wherein the source of radiation is modulated with at least one part of additional signals, and wherein in the additional unit the additional signals are separated from measurement signals of the detector by means of demodulation.

19. The process absorption spectrometer according to claim 14, wherein the unit containing the source of radiation contains means for generating a measurement result from measurement signals of the detector, and wherein the measurement signals are transmitted from the additional unit to the unit containing the source of radiation using the field bus.

20. The process absorption spectrometer according to claim 14, wherein the power is supplied to the first unit via the field bus and a power is supplied to the second unit via the field bus.

* * * * *